United States Patent [19]

Jones

[11] Patent Number: 5,225,672
[45] Date of Patent: * Jul. 6, 1993

[54] METHOD AND APPARATUS FOR DETECTING MOVEMENT OF AN ELECTRO-OPTICAL TRANSDUCER

[75] Inventor: Paul H. Jones, Mercer Island, Wash.

[73] Assignee: SpaceLabs Medical, Inc., Redmond, Wash.

[*] Notice: The portion of the term of this patent subsequent to Oct. 8, 2008 has been disclaimed.

[21] Appl. No.: 771,010

[22] Filed: Oct. 3, 1991

Related U.S. Application Data

[63] Continuation-in-part of Ser. No. 592,230, Oct. 3, 1990, Pat. No. 5,055,671.

[51] Int. Cl.$^5$ ................................. H01J 5/16
[52] U.S. Cl. ...................... 250/227.21; 128/667; 356/41
[58] Field of Search ................ 250/227.11, 227.21; 128/664–667; 356/39–42

[56] References Cited

U.S. PATENT DOCUMENTS

| | | | |
|---|---|---|---|
| 3,825,342 | 7/1974 | Lubbers et al. | 356/41 |
| 3,970,394 | 7/1976 | Stanton | 250/227.11 |
| 4,494,550 | 1/1985 | Blazek et al. | 128/664 |
| 4,854,699 | 8/1989 | Edgar, Jr. | 356/41 |
| 4,872,348 | 10/1989 | Curry | 73/653 |
| 5,055,671 | 10/1991 | Jones | 356/41 |

FOREIGN PATENT DOCUMENTS

| | | |
|---|---|---|
| 2559051A1 | 8/1985 | European Pat. Off. |
| 3230615A1 | 2/1984 | Fed. Rep. of Germany |
| 2050610A | 1/1981 | United Kingdom |
| 2230599A | 10/1990 | United Kingdom |

Primary Examiner—David C. Nelms
Assistant Examiner—S. Allen
Attorney, Agent, or Firm—Seed and Berry

[57] ABSTRACT

An apparatus for photo-optically detecting transducer motion using a photodetector resiliently suspended inside the transducer housing and photo-optically coupled to a light source. During movement the inertia effect of the photodetector along with the resilient suspension system causes the changes in the photo-optical coupling between the photodetector and the light source. The inertia effect of the photodetector is enhanced by adding a mass to the photodetector. Either the magnitude or the phase of the photodetector output is monitored to detect movement. In another embodiment, a light emitter is resiliently suspended so that movement induced changes in the position of the light emitter alter the coupling of light to one or more light detectors.

20 Claims, 8 Drawing Sheets

METHOD AND APPARATUS FOR DETECTING MOVEMENT OF AN ELECTRO-OPTICAL TRANSDUCER

CROSS-REFERENCE TO RELATED APPLICATION

This application is a continuation-in-part of U.S. application Ser. No. 07/592,230, filed Oct. 3, 1990 now U.S. Pat. No. 5,055,671.

FIELD OF THE INVENTION

The instant invention relates to movement detection. More particularly, the instant invention relates to an apparatus which detects transducer movement during photo-optical scanning.

DESCRIPTION OF THE PRIOR ART

Photoplethysmographs are well-known instruments for determining and registering variations in the blood volume present or passing through tissue using light sources. A specific application of photoplethysmography is non-invasive pulse oximetry, the measurement of arterial hemoglobin oxygen saturation.

Pulse oximeters have a transducer that is applied to a patient during measurement. This transducer has at least one light source, generally a light-emitting diode (LED), which transmits light through the patient's skin and into his subcutaneous tissues. A portion of the light is received by a photodetector and is converted into an electrical output called a working signal. The working signal may result from reflections of the light from the patient's tissue and blood, the reflective mode of operation, or it may result from light which has passed completely through the patient's tissue, the transillumination mode of operation. Ideally, the working signal varies only in response to changes in blood volume. However, transducer movements may affect the working signal by causing it to vary in response to transducer movement. This dependency on transducer movement, called motion artifact, is undesirable and can obscure the variations caused by blood volume changes.

Motion artifact is well known, and pulse oximeter manufacturers have taken steps to reduce its effects. However, these steps are generally ineffective unless the transducer movement is first detected, something that is particularly difficult to do when the motion artifact occurs in conjunction with the patient's pulse.

It is clear that there has existed a need for a simple, low-cost apparatus for detecting transducer movement.

SUMMARY OF THE INVENTION

It is an object of the present invention to provide an apparatus and method for detecting transducer movement.

To achieve the foregoing object and others, the present invention detects transducer movement by (1) amplifying changes in the photo-optical coupling between a photodetector and a light source, and (2) detecting the transducer movement by monitoring the changes in the photo-optical coupling. In a better embodiment, three photodetectors are elastically mounted so that transducer movement changes the photo-optical coupling between the light source and each photodetector differently. Preferably, the three photodetectors are mounted symmetrically on a circular, plate with different masses attached to each photodetector.

DETAILED DESCRIPTION OF THE PREFERRED EMBODIMENT

Figure 1:
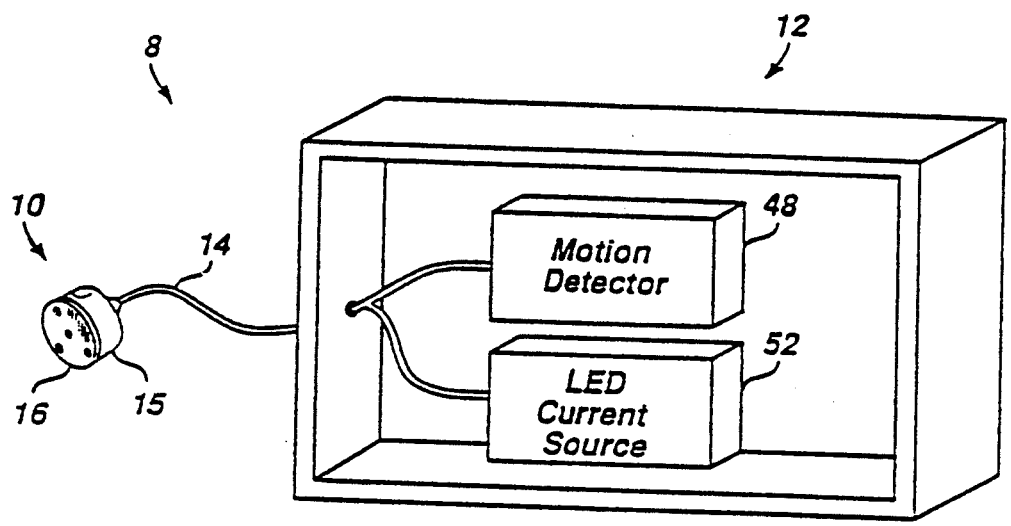
FIG. 1 is a simplified isometric view of a motion detector according to the preferred embodiment of the present invention.

With reference to FIG. 1, a pulse oximeter 8 according to the preferred embodiment includes a transducer 10, a pulse oximeter chassis 12, and a cable 14. The operation and description of these assemblies is described below.

Figure 2:
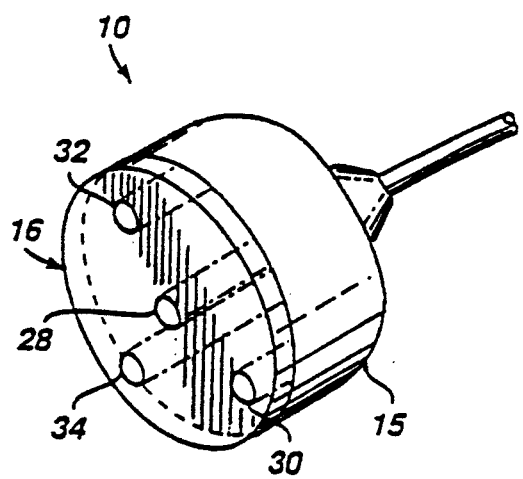
FIG. 2 is an isometric view of one embodiment of the inventive motion transducer.

Referring now to FIG. 2, the transducer 10 has a housing 15 with a circular, plate 16 as a bottom surface. The plate 16 contacts a patient during pulse oximetry. The transducer housing 15 is preferably rigid, except for the plate 16, to support and protect the components within the transducer 10. In operation, the transducer 10 is maintained in a relatively fixed position on a patient by use of adhesive tape (not shown).

Figure 3:
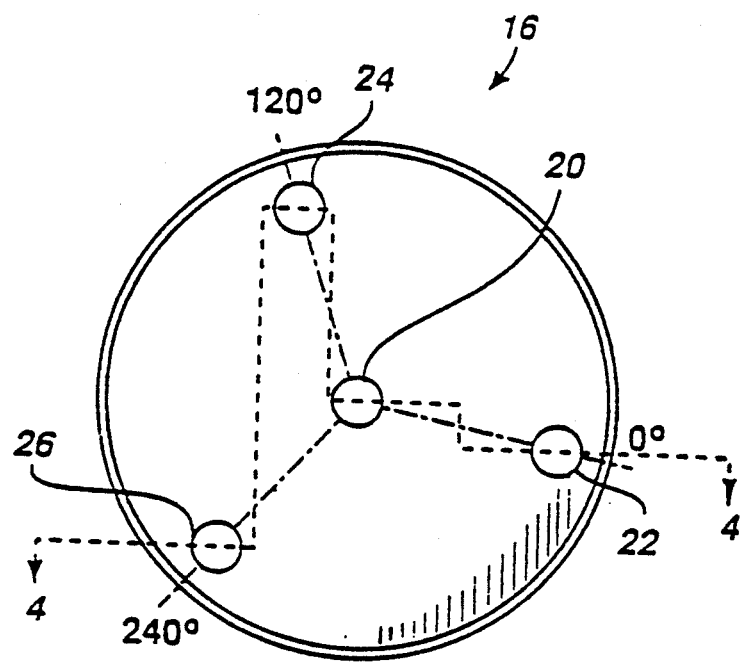
FIG. 3 is a bottom view of a plate used in the transducer of FIG. 2.

The plate 16, best illustrated in FIG. 3, is ideally made from a resilient, flexible material that supports holes without tearing and has good adhesive properties with an adhesive compound 18 used to mount components. However, a rigid plate 16 would also work, albeit with less desirable results. While the preferred material for plate 16 is silicon rubber, other materials are suitable and will be well known to those in the art. Likewise, numerous materials are suitable for the construction of the transducer housing 15.

Referring again to FIG. 3, a centrally located LED opening 20 is disposed through the plate 16. Additionally, the plate 16 has symmetrical concentric openings: 0° opening 22, 120° opening 24, and 240° opening 26 disposed through it. These openings are preferably located about two-thirds of the way between the center and outer periphery of the plate 16. They are named for their angular positions relative to the 0° opening 22, which, because of symmetry, is selectable at random. All openings are easily formed using conventional methods such as a hole punch.

Figure 4:
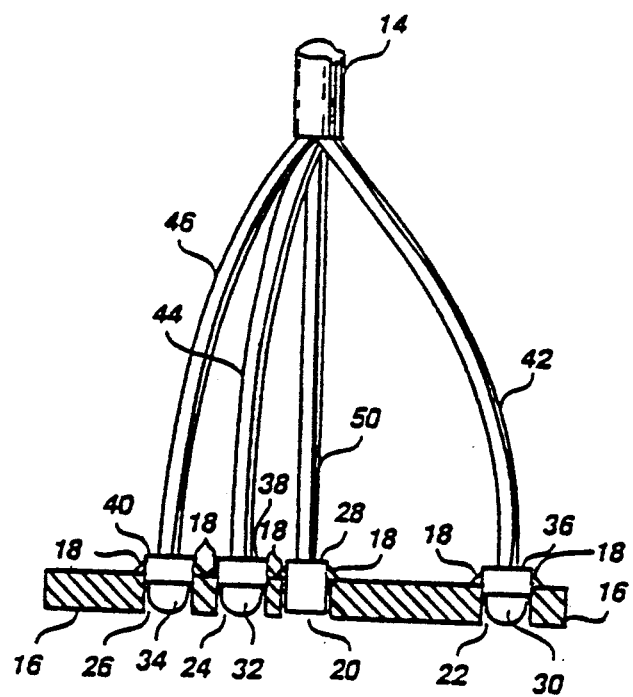
FIG. 4 is a cross-sectional view taken along the line 4—4 of FIG. 3.

Referring now to FIG. 4, a cross-sectional view of FIG. 3 taken along lines 4—4, a light-emitting diode 28 is attached to the plate 16 in the LED opening 20. Similarly, a 0° photodetector 30, a 120° photodetector 32, and a 240° photodetector 34 are attached to the plate 16 in the 0° opening 22, the 120° opening 24, and the 240° opening 26, respectively. Attachment of these components to the plate 16 is performed by the adhesive compound 18, previously mentioned.

The photodetectors 30, 32, and 34 are preferably silicon photodiodes, but other photodetectors, such as photodiodes made from other semiconductor compounds, phototransistors, or photoresistors, are also suitable. Similarly, while the light source (light-emitting diode 28 in the preferred embodiment) is preferably a light-emitting diode, other light sources, such as a laser or an incandescent bulb, could also be used. Whatever embodiments are chosen, the photodetectors must create sufficient working signals from light from the light source for system operation.

Referring again to FIG. 4, a 0° mass 36, a 120° mass 38, and a 240° mass 40 are rigidly attached to the 0° photodetector 30, the 120° photodetector 32 and the 240° photodetector 34, respectively. Each mass is preferably unique in magnitude and is attached to its photodetector by the adhesive compound 18.

Figure 5:
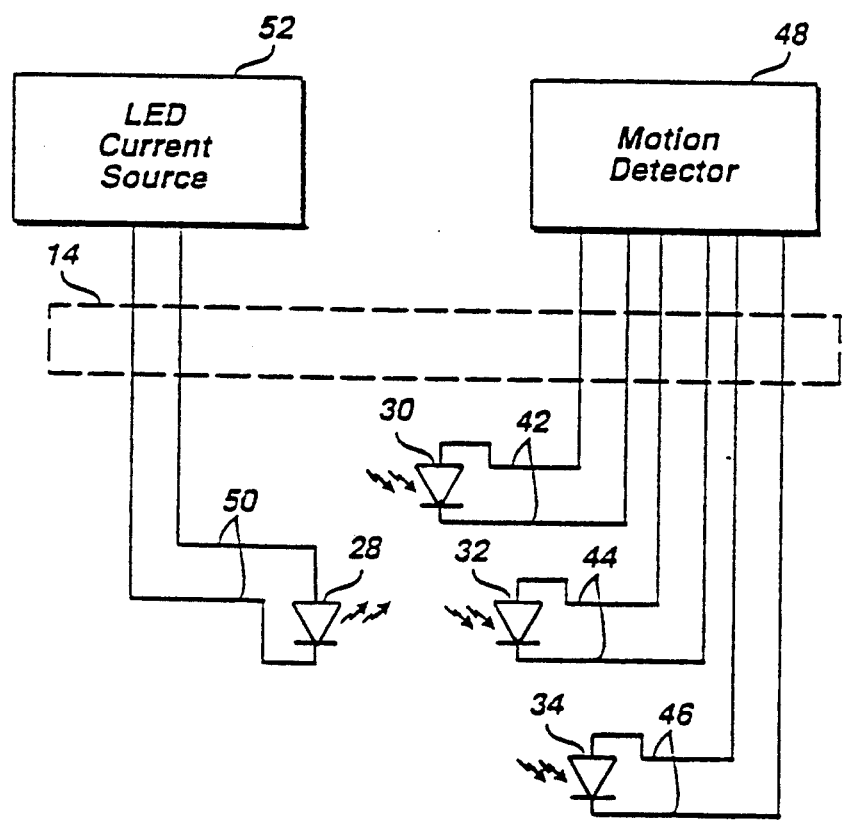
FIG. 5 is a partial schematic diagram, partial block diagram of one embodiment of the inventive motion sensor used as part of a pulse oximeter.

Referring now to FIGS. 1, 4, and 5 as required, the 0° photodetector 30, the 120° photodetector 32, and the 240° photodetector 34 have leads 42, 44, and 46, respectively, which, via the cable 14, electrically connect to a motion detector network 48. Also, cable 14 connects the light-emitting diode 28 having leads 50 to an LED current source 52. The motion detector network 48 and the LED current source 52 are both within the pulse oximeter chassis 12.

Referring now to FIG. 5, the LED current source 52 injects current into the light-emitting diode 28, causing it to emit light. Some of the light from the light-emitting diode 28 reflects from the patient's subcutaneous tissues and returns to the 0° photodetector 30, the 120° photodetector 32, and the 240° photodetector 34, creating working signals. These working signals are applied to the motion detection network 48 which is able to detect changes to the proportionality and/or phase relationships of the working signals.

Figure 6:
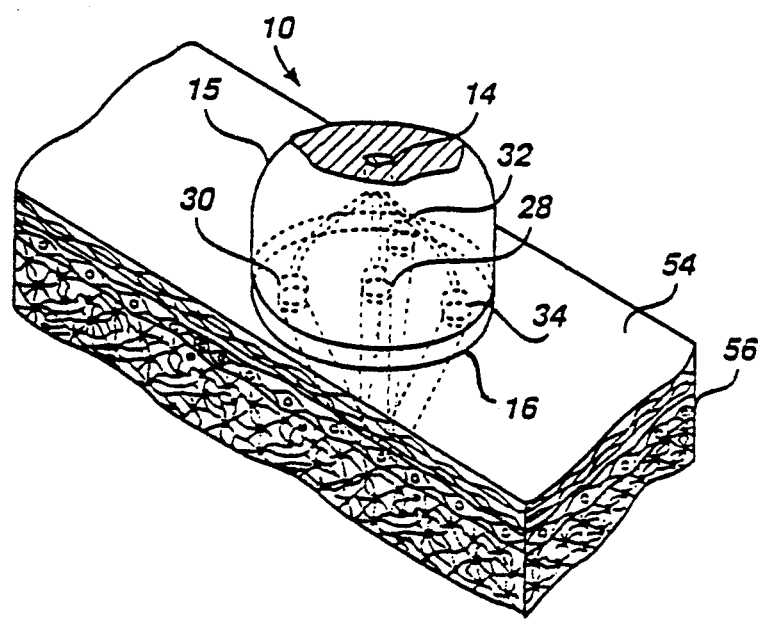
FIG. 6 is an operational diagram of the transducer of FIG. 2 attached to a patient.

System operation can be understood by referring to FIGS. 4, 5, and 6 as required while reading the following discussion. With the transducer 10 contacting the patient's skin 54, the LED current source 28 causes the light-emitting diode 28 to emit light which penetrates the patient's skin. Some of this light reflects from the patient's subcutaneous tissue 56 onto the photodetectors 30, 32, and 34, creating working signals. While these working signals are not, in general, the same, they are substantially stable and maintain their relative relationships as long as the photo-optical couplings between the light-emitting diode 28 and the photodetectors 30, 32, and 34 remains constant.

Movement of the transducer 10 changes the light paths and the photo-optical couplings between the light-emitting diode 28 and the photodetectors 30, 32, and 34. The photo-optical coupling changes are enhanced by the resilient suspension system formed by the plate 16, the photodetectors 30, 32, and 36, and the masses 36, 38, and 40. Inertia effects during transducer acceleration causes each photodetector/mass combination to move the plate 16 differently. This causes each working signal to change differently. The working signal differences are then detected by the motion detector 48. Once transducer movement is detected, various methods such as corrective mathematical algorithms or simply disabling measurement during movement may be used to reduce the effects of motion artifact.

While preferably three photodetectors are used, it is possible to detect transducer movement with as few as one photodetector. Assuming, for convenience, that a photodetector is mounted with a mass on a flexible plate, transducer acceleration would cause the plate to flex, causing changes in the photo-optical coupling. However, detecting these changes is difficult since the working signal can only use itself as a reference.

Using two photodetectors substantially improves movement detection since changes can be detected by comparing working signals to each other. However, transducer movement can occur such that the relationships between the working signals do not change, despite changes in the photo-optical couplings. To understand this, consider movement in a direction perpendicular to a line between the two photodetectors. Ideally, any changes in the two working signals would be common to both and thus detecting changes by comparing the two working signals would not detect movement. While actual working signal changes are more complicated than that suggested, it is nevertheless not believed possible to guarantee detection of all movements with only two photodetectors.

However, adding a third photodetector allows for simple detection of movement in any direction, except possibly the Z-axis (perpendicular to the plane containing all three photodetector). A comparison of the amplitudes or phases of the working signal at any photodetector with those of the other two photodetectors will detect motion. The problem with Z-axis movement detection is that if all suspension system are the same, then Z-axis movement will causes the same photo-optical coupling changes. This problem is overcome by making each photodetector suspension system different. In the preferred embodiment, each photodetector suspension system is made different by adding different masses to each photodetector.

Figure 7:
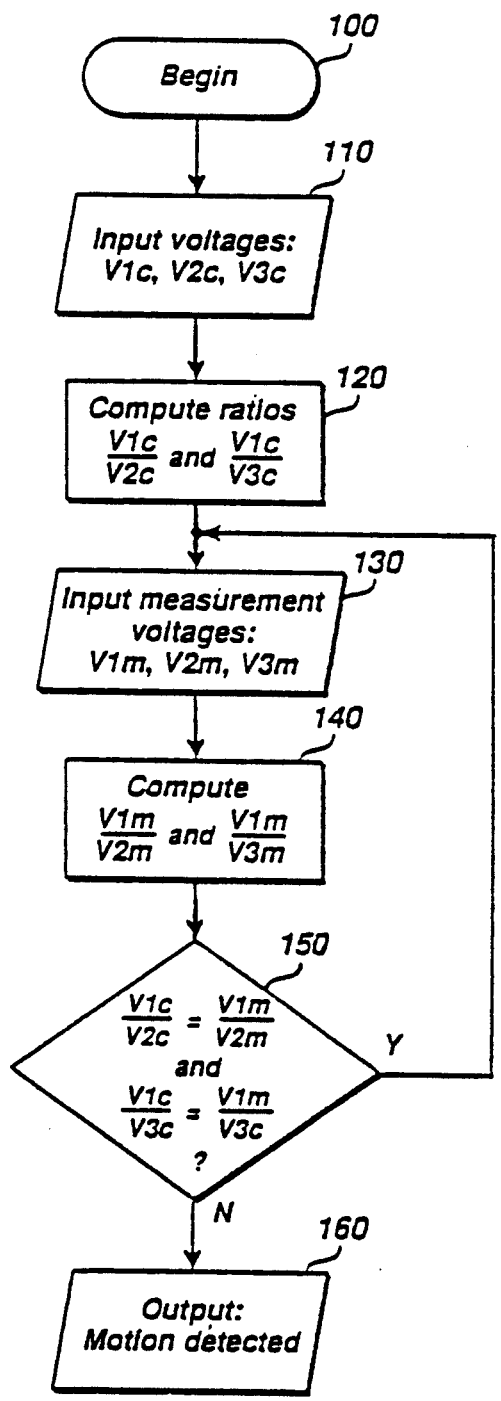
FIG. 7 is a flow chart depicting one method of programming a computer to sense transducer motion from changes in the working signals.

A method of detecting changes in the proportionality and/or phase relationships of the working signals is illustrated by the flow diagram of FIG. 7. This method will work equally well with changes in the working signals' phase relationships or voltages. For convenience, FIG. 7 will be discussed in terms of changes in working signal voltages. In block 100, motion detection begins. At a calibration time, the voltage outputs from the motion detector 48, resulting from working signals from the 0° photodetector 30, the 120° photodetector 32, and the 240° photodetector 34 are stored as voltages V1c, V2c, and V3c, respectively, as indicated in block 110. These voltages are used as shown in block 120, to compute two ratios, the first ratio being V1c÷V2c, and V1c+V3c. These ratios are stored for later use. Subsequent voltages from the motion detector 48, corresponding to the working signals from the 0° photodetector 30, the 120° photodetector 32, and the 240° photodetector 34 are input as measurement voltages V1m, V2m, and V3m, respectively, as indicated in block 130. These voltages are used to compute, as shown in block 140, two additional ratios, V1m÷V2m, and V1m÷V3m. As shown in block 150, motion is sensed by comparing the ratio (V1c÷V2c) to the ratio (V1m÷V2m), and the ratio (V1c÷V3c) with the ratio (V1m÷V3m). If the equated ratios are the same, the transducer 10 has not moved. However, if one or both of the equated ratios are unequal, then it is known that the transducer 10 has moved. If the ratios have not changed, the new input measurement is taken and new ratios are computed, and the operation of block 150 is repeated. However, if motion has occurred, then as shown in block 160, a signal is output showing that transducer motion has occurred. The calibration voltages V1c, V2c, and V3c can be updated at fixed times, or they can be updated continuously with the last values of V1m, V2m, and V3m, respectively.

It should be understood that the flex plate/photodetector/mass arrangement of the preferred embodiment is not unique and other arrangements can achieve the same results. For example, the masses could under some circumstances be eliminated, or they could be mounted directly on the plate near the photodetectors, or the photodetectors could be mounted on a spring suspension system instead of a plate. Also, while the preferred embodiment has the LED 28 and photodetectors 30, 32, 34 all resiliently mounted, it will be understood that just the LED 28 and/or less than all of the photodetectors may be resiliently mounted.

Figure 8:
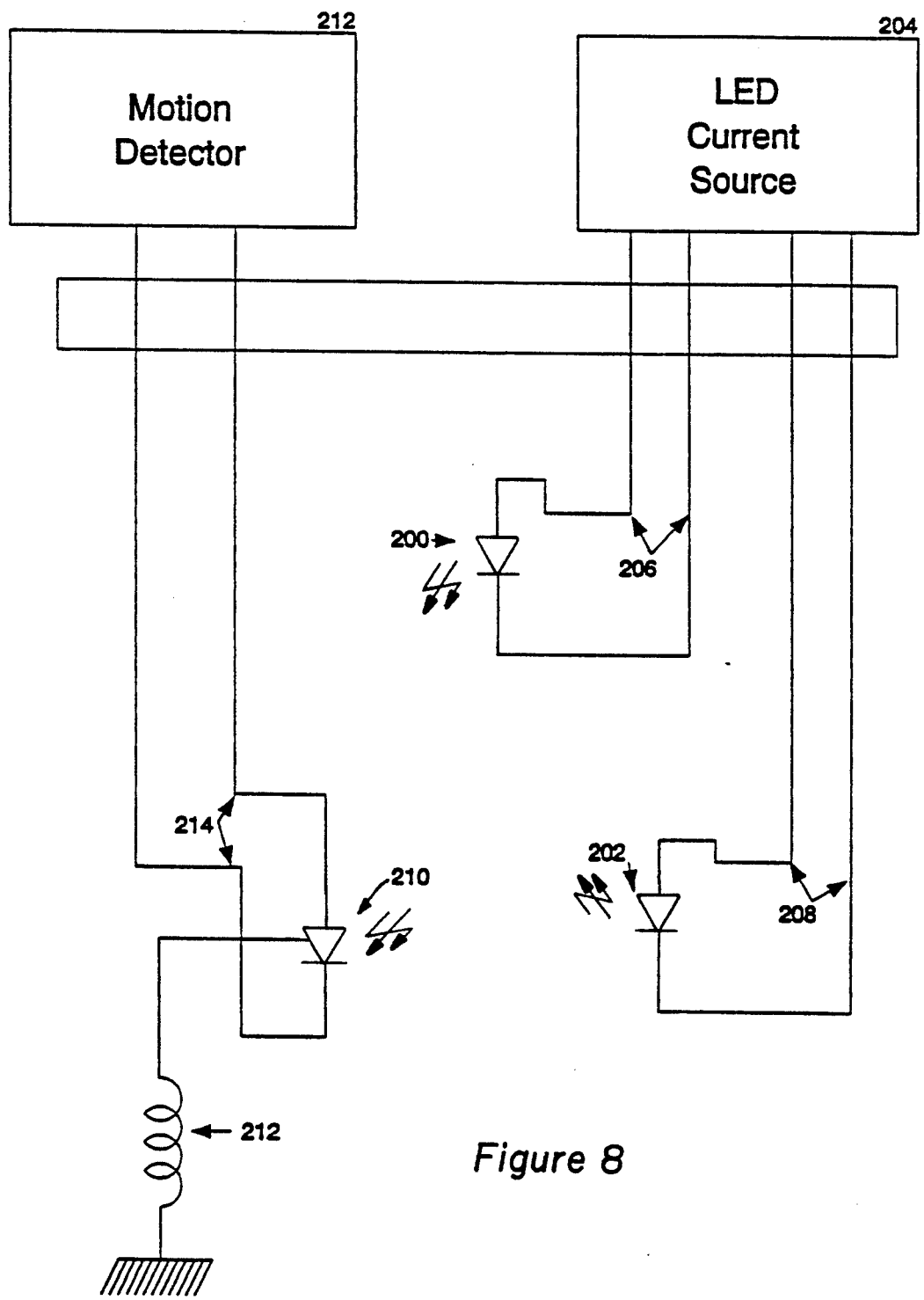
FIG. 8 is a partial schematic, partial block diagram of another embodiment of a motion sensor.

The basic concept of the inventive system is to couple light along two paths from a first type of electro-optical transducer, such as a light-emitting diode, and two electro-optical transducers of a second type, such as light detectors, and then vary the coupling along one of the paths by resiliently mounting one of the electro-optical transducers. In the embodiment of FIGS. 1-7, light is coupled from a single LED 28 to two or more photodetectors 30-34. However, several alternative embodiments for implementing the basic concept of the invention are possible. With reference to FIG. 8, two light-emitting diodes 200, 202 are connected to a conventional LED current source 204 through respective leads 206, 208. Light is coupled from each of the LEDs 200, 202 to a single photodetector 210 which is connected to a motion detector circuit 212 through a pair of leads 214. In the embodiment of FIG. 8, the photodetector 210 is resiliently mounted through a conventional elastic suspension system which is schematically illustrated at 212 in FIG. 8.

In operation, the LEDs 200, 202 are alternately illuminated by the LED current source 204 so that the magnitude of the coupling of light from the LED 200 to the photodetector 210 can be measured alternately with the coupling of light from the LED 202 to the photodetector 210. When the transducer is not moving, the coupling from each of the LEDs 200, 202 to the photodetector 210 is relatively constant. As a result, the difference in the coupling from the LED 200 to the photodetector 210 and the coupling from the LED 202 to the photodetector 210 is relatively stable. However, when the transducer moves, acceleration induced forces applied to the photodetector 210 (which may be coupled to a weight not shown) causes the photodetector 210 to move within its elastic suspension 212. As a result, the magnitude of the coupling from the LED 200 to the photodetector 210 and the coupling from the LED 202 to the photodetector 210 varies. Although the coupling from both LEDs 200, 202 to the photodetector 210 vary, the coupling from the LED 200 does not vary in the same manner as the coupling from the LED 202. As a result, the comparison of the coupling from the LED 200 to the photodetector 210 with the coupling from the LED 202 to the photodetector 210 varies and is detected by the motion detector 212.

Figure 9:
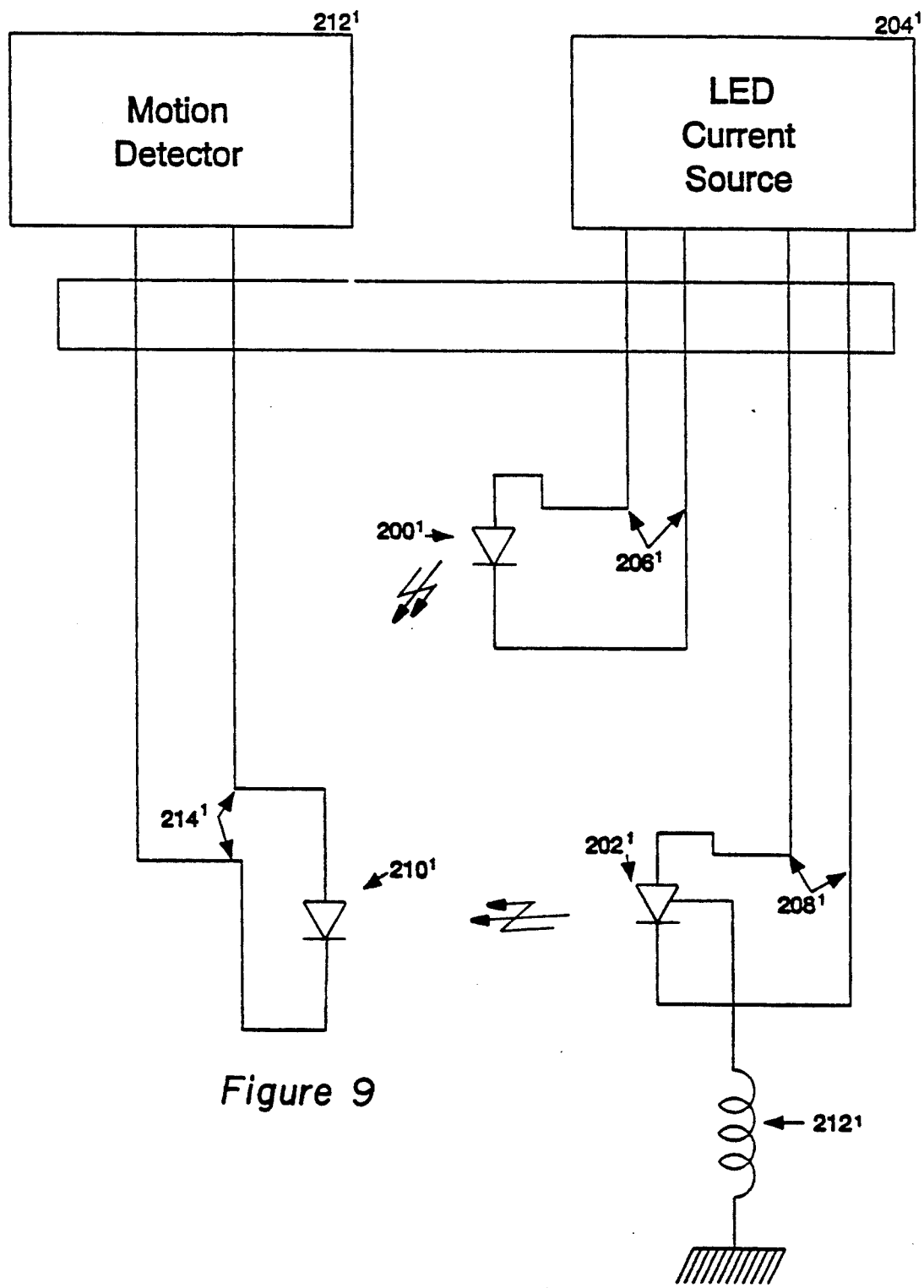
FIG. 9 is a partial schematic, partial block diagram of another embodiment of a motion sensor.

Another embodiment, illustrated in FIG. 9, uses a single photodetector 210' and two LEDs 200', 202' as in the embodiment of FIG. 8. However, unlike the embodiment of FIG. 8, the embodiment of FIG. 9 utilizes an LED 32 that is resiliently mounted using a conventional elastic suspension 212'.

In operation, the LEDs 200', 202' are alternately illuminated in the same manner as in the embodiment of FIG. 8. However, in the embodiment of FIG. 9, the coupling from the LED 200' to the photodetector 210' remains constant. However, the coupling from the LED 202' mounted with the elastic suspension 212' to the photodetector 210' varies as the LED 202' undergoes acceleration induced movement. Thus, a comparison of the coupling from LED 200' to photodetector 210 with the coupling from LED 202' to photodetector 210' varies when the transducer is undergoing motion.

Figure 10:
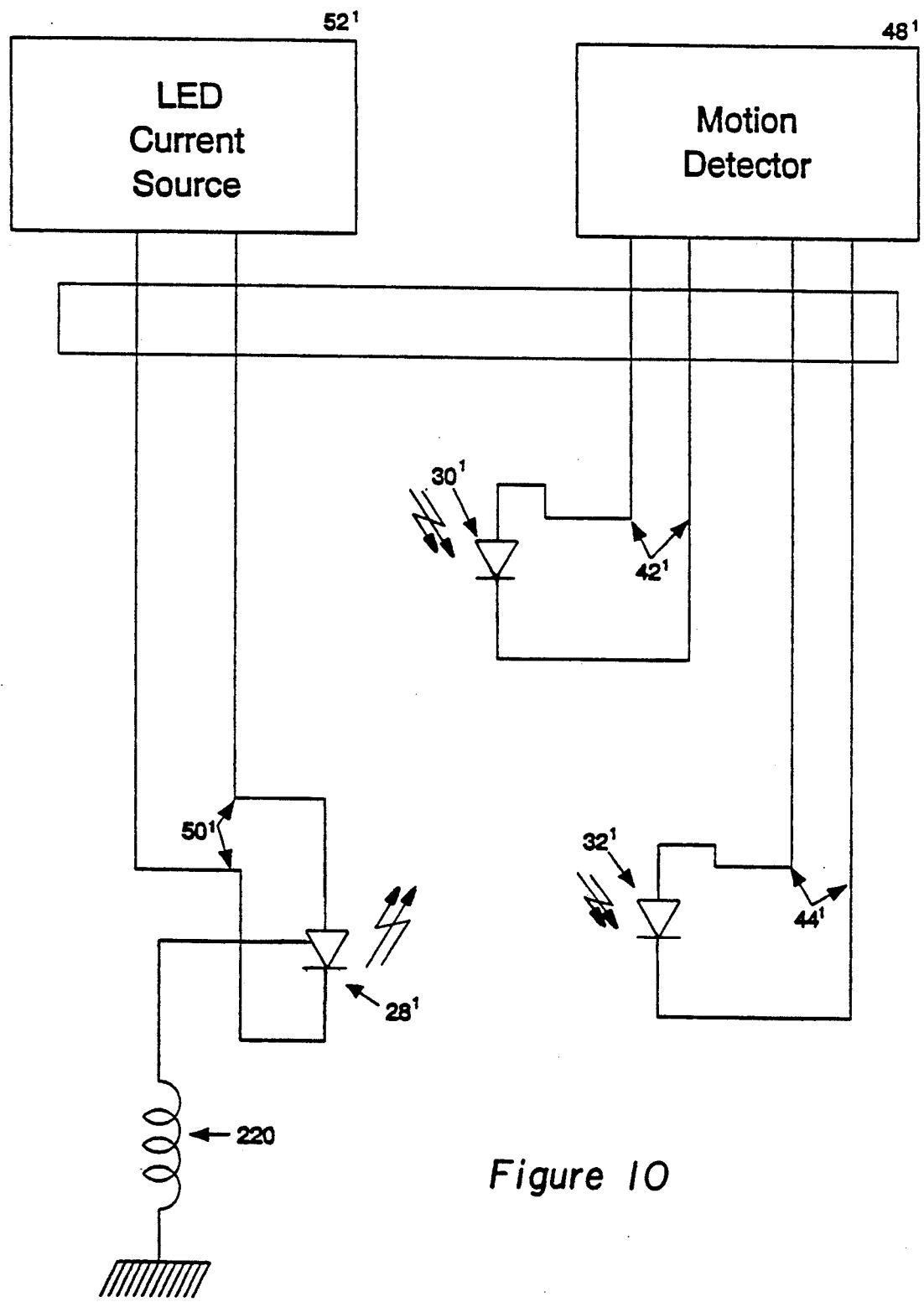
FIG. 10 is a partial schematic, partial block diagram of still another embodiment of a motion sensor.

A final embodiment of the inventive motion sensor is illustrated in FIG. 10. The embodiment of FIG. 10 differs from the embodiment of FIGS. 8 and 9 is similar to the embodiment of FIG. 5 in that it utilizes a single LED 28' and a pair of photodetectors 30', 32'. The LED 28' is connected to an LED current source 52' through a pair of leads 50'. The photodetectors 30', 32' are connected to a motion detector 48' through respective pairs of leads 42', 44'. The embodiment of FIG. 10 differs from the embodiment of FIGS. 1-7 in that instead of resiliently mounting one or more of the photodetectors 30', 32', the embodiment of FIG. 10 utilizes a LED 28' that is resiliently mounted by an elastic suspension shown schematically as 220 in FIG. 10. In operation, the coupling of light from the LED 28' to each of the photodetectors 30', 32' is relatively stable when the transducer is nonmoving. However, motion of the transducer causes the LED 28' to move thereby varying the coupling to each of the photodetectors 30', 32'. However, the coupling of light from the LED 28' to the photodetector 30' does not vary in the same manner as the coupling from the LED 28' to the photodetector 32'. As a result, comparison of the outputs from the photodiodes 30', 32' varies when the transducer is moving.

It is thus seen that there are several different techniques for carrying out the basic concept of providing a pair of light paths between three or more electro-optical transducers and varying the magnitude of the coupling through at least one of the paths by resiliently mounting one or more of the electro-optical transducers.

I claim:

1. A motion sensor, comprising:
a first electro-optical transducer converting between electricity and light in one direction;
a second electro-optical transducer converting between electricity and light in a direction opposite the conversion direction of said first electro-optical transducer, said second electro-optical transducer being optically coupled to said first electro-optical transducer;
a third electro-optical transducer converting between electricity and light in the same direction as said second electro-optical transducer, said third electro-optical transducer being optically coupled to said first electro-optical transducer;
means for resiliently mounting at least one of said electro-optical transducers so that at least one of said electro-optical transducers is displaced by acceleration imparted to said transducer thereby modulating the light optically coupled between said first electro-optical transducer and at least one of said second and third electro-optical transducers; and means for comparing a characteristic of the light coupled between said first electro-optical transducer and said second electro-optical transducer with a characteristic of the light coupled between said first electro-optical transducer and said third electro-optical transducer whereby movement of said transducer is detected by variations in the characteristic of light coupled between said first electro-optical transducer and at least one of said second and third electro-optical transducers.

2. The motion sensor of claim 1 wherein said first electro-optical transducer is resiliently mounted so that the light coupled between said first electro-optical transducer and both said second and third electro-optical transducers vary with sensor movement.

3. The motion sensor of claim 2 wherein said first electro-optical transducer is a light detector, and wherein said second and third electro-optical transducer are light emitters.

4. The motion sensor of claim 2 wherein said first electro-optical transducer is a light emitter, and wherein said second and third electro-optical transducers are light detectors.

5. The motion sensor of claim 1 wherein said second electro-optical transducer is resiliently mounted so that the light coupled between said first electro-optical transducer and both said second and third electro-optical transducer varies with sensor movement.

6. The motion sensor of claim 5, further including means for resiliently mounting said third electro-optical transducer so that said third electro-optical transducer is also displaced by acceleration imparted to said transducer.

7. The motion sensor of claim 1 wherein said first electro-optical transducer is a light detector, and wherein said second and third electro-optical transducers are light emitters.

8. The motion sensor of claim 1 wherein respective weights are physically coupled to each resiliently mounted electro-optical transducer to amplify the acceleration induced displacement of said electro-optical transducers.

9. The motion sensor of claim 1 wherein a plurality of said electro-optical transducers are resiliently mounted, and wherein said means for resiliently mounting said electro-optical transducers provides each of said resiliently mounted transducers with suspension characteristics that are different from the suspension characteristics provided to the other of said electro-optical transducers thereby increasing the differences between the acceleration induced movement of each of said electro-optical transducers.

10. The motion sensor of claim 9 wherein respective weights of different mass are physically coupled to each of said resiliently mounted electro-optical transducers to provide said resiliently mounted electro-optical transducers with different suspension characteristics.

11. The motion sensor of claim 1 wherein said second and third electro-optical transducers are positioned symmetrically around said first electro-optical transducer.

12. The motion sensor of claim 1 wherein said means for resiliently mounting said electro-optical transducer includes a resilient plate on which said resiliently mounted electro-optical transducer is mounted.

13. The motion sensor of claim 1 wherein the optical coupling between from said first electro-optical transducer and said second electro-optical transducer is further modulated by a medical parameter so that light coupled between said first electro-optical transducer and at least one of said second and third electro-optical transducers is used to sense said medical parameter and to sense movement.

14. The motion sensor of claim 1 wherein the characteristic of the light that is compared by said means for comparing is the intensity of light coupled between said first electro-optical transducer and said third electro-optical transducer.

15. A method of sensing movement of a transducer having an electro-optical transducer of a first type converting between electricity and light in one direction, and a pair of electro-optical transducer, of a second type optically coupled to said first type of electro-optical transducer, said second type of electro-optical transducers converting between electricity and light in a direction opposite the conversion direction of said first type of electro-optical transducer, said method comprising:

resiliently mounting at least one of said electro-optical transducers in said transducer so that said resiliently mounted electro-optical transducer is displaced by acceleration imparted to said transducer thereby modulating the light optically coupled between said first type of electro-optical transducer and said second type of electro-optical transducer; and comparing a characteristic of the light coupled between said first electro-optical transducer and one of said second electro-optical transducers with a characteristic of the light coupled between said first electro-optical transducer and the other of said second electro-optical transducers so that movement of said transducer is indicated by variations in the differences between said characteristics.

16. The method of claim 15 wherein said first type of electro-optical transducer is resiliently mounted.

17. The method of claim 15 wherein said first type of electro-optical transducer is a light detector, and wherein said second type of electro-optical transducer is a light emitter.

18. The method of claim 17, further including the step of alternately illuminating said light emitters to separately determine the magnitude of light coupled from said light emitter to said light detector.

19. The method of claim 15 wherein the optical coupling between said first type of electro-optical transducer and at least one of said second type of electro-optical transducers is further modulated by a medical parameter, and wherein said method further includes using a characteristic of the coupling between said first type of electro-optical transducer and said second type of electro-optical transducer to sense said medical parameter and to sense movement of said transducer.

20. The method of claim 15 wherein said second type of electro-optical transducers are positioned symmetrically around said first type of electro-optical transducer.

* * * * *